United States Patent
Amalric et al.

(10) Patent No.: US 7,514,496 B2
(45) Date of Patent: Apr. 7, 2009

(54) EMULSIONS OF WATER-IN-OIL TYPE, WITH A HIGH CONTENT OF AQUEOUS PHASE, THEIR PROCESS OF PREPARATION AND THEIR USES

(75) Inventors: Chantal Amalric, Blan (FR); Alicia Roso, Saix (FR); Guy Tabacchi, Paris (FR)

(73) Assignee: Societe d'Exploitation de Produits pour les Industries Chimiques (Seppic), Paris (FR)

( * ) Notice: Subject to any disclaimer, the term of this patent is extended or adjusted under 35 U.S.C. 154(b) by 77 days.

(21) Appl. No.: 10/799,373

(22) Filed: Mar. 12, 2004

(65) Prior Publication Data

US 2005/0101727 A1    May 12, 2005

(30) Foreign Application Priority Data

Mar. 14, 2003 (FR) .................................. 03 03157
Sep. 25, 2003 (FR) .................................. 03 11263

(51) Int. Cl.
 *A61K 8/06* (2006.01)
 *A61K 8/81* (2006.01)
 *A61Q 17/04* (2006.01)
(52) U.S. Cl. ....................... 524/501; 524/801
(58) Field of Classification Search ................. 524/501, 524/801
See application file for complete search history.

(56) References Cited

U.S. PATENT DOCUMENTS

| | | | |
|---|---|---|---|
| 5,304,334 A | * | 4/1994 | Lahanas et al. ............... 516/23 |
| 5,306,498 A | * | 4/1994 | Vesperini et al. ............ 424/401 |
| 5,746,945 A | | 5/1998 | Ryklin et al. |
| 5,952,395 A | * | 9/1999 | Lorant .................... 514/772.4 |
| 6,042,815 A | * | 3/2000 | Kellner et al. ................. 424/63 |
| 6,149,900 A | * | 11/2000 | Afriat et al. .............. 424/78.03 |
| 6,667,396 B2 | | 12/2003 | Milius et al. |

FOREIGN PATENT DOCUMENTS

| | | |
|---|---|---|
| EP | 0 503 853 A2 | 3/1992 |
| EP | 1 142 901 | 3/2001 |
| EP | 1 325 729 A2 | 12/2002 |
| FR | 2 816 836 A1 | 11/2000 |
| WO | WO 97 40814 | 4/1997 |
| WO | WO 02 41867 A1 | 5/2002 |

OTHER PUBLICATIONS

R. Pons, et al.: "Novel preparation methods for highly concentrated water-in-oil emulsions", Colloids And Surfaces A: Physicochemical and Engineering Aspects, vol. 91, 1994, pp. 259-266, XP008026972.

* cited by examiner

*Primary Examiner*—Kelechi C Egwim
(74) *Attorney, Agent, or Firm*—Young & Thompson

(57) ABSTRACT

A composition and its method of production, wherein the composition includes both an oily external phase and a gelled aqueous phase, wherein the aqueous phase is 60 to 98% by weight of the total composition. Additional features of the composition include the aqueous phase containing a polyelectrolyte in which the ionic sites are combined with their counter-ions. The oily phase of the composition contains one or more oils and also an emulsifying system with a lipophilic nature. The composition may be utilized in the following applications: cosmetic, pharmaceutical, veterinary, or detergent preparations.

15 Claims, No Drawings

EMULSIONS OF WATER-IN-OIL TYPE, WITH A HIGH CONTENT OF AQUEOUS PHASE, THEIR PROCESS OF PREPARATION AND THEIR USES

A subject-matter of the present invention is emulsions of water-in-oil type, with a high content of aqueous phase, their process of preparation and their uses.

This application claims the benefit of priority under 35 U.S.C. § 119(a) and (b) 1 to French application No. 03 03157, filed Mar. 14, 2003, and French application No. 03 11263, filed Sep. 25, 2003, the entire contents of which are incorporated herein by reference.

BACKGROUND

Emulsions make it possible to simultaneously convey water-soluble and fat-soluble substances and thus find an application in particular in the cosmetics, pharmaceutical and veterinary fields and in the field of detergents.

In the cosmetics field, there exists a requirement on the part of the user of products in the form of emulsions to have available emulsions which exhibit appropriate sensory characteristics. Emulsions which provide a feeling of freshness and which are felt to be non-"sticky" when applied to the skin are particularly desired.

Emulsions are categorized according to the nature of the continuous phase (also referred to as "external phase") in which droplets of the other phase (referred to as "internal phase") are dispersed.

In the case where the oil droplets are dispersed in an aqueous continuous phase, the system is called an emulsion of "oil-in-water" (O/W) type.

In the case where the water droplets are dispersed in an oily continuous phase, the emulsion is of "water-in-oil" (W/O) type.

Generally, among these two types of emulsions, it is easier to manufacture emulsions of oil-in-water (O/W) type as emulsions of W/O type are intrinsically unstable thermodynamically. This is because, if equal amounts of water and of oil are mixed, the formation of an emulsion with an aqueous continuous phase is always observed as the cohesive forces between water molecules are stronger than those between oil molecules.

Nevertheless, emulsions with an oily continuous phase (W/O) exhibit numerous advantages:

the separation between the water droplets reduces the possibility of growth of microorganisms. The use of antiseptics, essential when the continuous phase is aqueous, may be avoided;

they keep well at low temperature, being much less sensitive in this respect than emulsions of O/W type;

the oily continuous phase covers the skin and protects it from dehydration and from external substances.

In the development of an emulsion system with an oily continuous phase, two types of modifications have been envisaged:

modifications of a mechanical nature regarding the combining of the phases (order of addition of the phases, control of the flow rate during the combining of the phases, temperature of the phases, rate of stirring, and the like);

modifications with regard to the chemical constituents having the result of stabilizing the emulsion.

As regards the modifications of a mechanical nature, the operating procedures employed for preparing W/O emulsions generally require:

a) a high energy input in the form of thermal activation (the aqueous and fatty phases are typically heated to 80° C.), which sometimes has to be followed by well-controlled gradual cooling; and/or b) the creation of turbulence in the two-phase medium to be emulsified (high rate of stirring (thousands of revolutions per minute) and high shear brought about by specific geometries of the stirrers).

As regards the modifications of a chemical nature, mention may be made of:

a) the use of microcrystalline waxes, such as ozokerite, which absorb the oil and prevent it from being exuded;

b) the use of liquid paraffins as fatty phase as these paraffins are easier to emulsify;

c) the addition of inorganic salts, such as, in particular, sodium chloride or magnesium chloride, making it possible to increase the cohesion of the interfacial film.

U.S. Pat. No. 5,746,945 discloses emulsions of water-in-oil type which are stabilized by an emulsifying system having two components: a) a polysiloxane/polyalkyl/polyether copolymer, and b) a phthalic anhydride derivative (a monoamide). The method of preparation of emulsions in this document consists of the gradual addition of the aqueous phase to the oily phase. The two phases are heated, each independently of the other, to 160 to 165° F. (71 to 74° C.) before being combined to produce the emulsion.

The document WO 97/40814 discloses W/O emulsions intended in particular to be used to impregnate baby wipes. The organic phase of the emulsions necessarily comprises a wax. The emulsifiers used are of carboxylic acid type, which are substituted by hydrocarbons, or ABA block copolymers, involving monomers such as 12-hydroxystearic acid and ethylene glycol, or an alkyl dimethicone copolyol. As regards the process used to prepare the emulsions, the fatty phase and the aqueous phase are typically heated to 160° F. (71° C.) and then they are mixed at this temperature to produce the emulsion.

The typical procedures of the prior art thus exhibit a number of disadvantages related in particular to the need to provide a significant energy input to produce the emulsion.

One problem to be solved thus consists in providing W/O emulsions with a high content of aqueous phase which exhibit in particular a fresh and nonsticky texture.

Another problem to be solved consists in making available a process for the preparation of such emulsions which is:

simple, that is to say that the number of stages employed is reduced and that factors such as the exact control of the flow rates for introducing the phases are not critical for the satisfactory operation of the process, and economical, that is to say that it is not necessary to expend a great deal of energy, either in heating the phases to be combined or in the vigorous stirring to be provided during the preparation of the emulsion.

SUMMARY

It has now been discovered, and this is the basis of the present invention, that, by adding an oily phase to a gelled aqueous phase, it is possible to obtain W/O emulsions having the abovementioned characteristics without significant thermal and mechanical input.

According to a first aspect, a subject-matter of the present application is thus an emulsion composed of an oily external phase and of a gelled aqueous phase, the said aqueous phase representing from 60 to 98% by weight, preferably from 80 to 98% by weight, of the composition, characterized in that:

the aqueous phase comprises a polymer of poly-electrolyte type, the ionic sites of which are combined with their counterions, and the oily phase comprises one or more oils and an emulsifying system with a lipophilic nature comprising one or more emulsifying surfactants.

According to a second aspect, a subject-matter of the present application is a process for the preparation of an emulsion of water-in-oil type with a high content of aqueous phase comprising the following stages:

a) a fatty phase comprising one or more oils is prepared in the presence of an emulsifying system with a lipophilic nature comprising one or more emulsifying surfactants;

b) a gelled aqueous phase comprising a polymer of poly-electrolyte type is prepared, independently of the fatty phase;

c) the fatty phase is added to the aqueous phase.

According to a third aspect, a subject-matter of the present application is cosmetic, pharmaceutical, veterinary or detergent preparations comprising an emulsion as defined above.

DESCRIPTION OF PREFERRED EMBODIMENTS

In accordance with the process of the invention, the preparation is carried out, in a first step, of a fatty phase comprising one or more oils chosen in particular from:

oils of vegetable origin, such as sweet almond oil, coconut oil, monoi oil, castor oil, jojoba oil, olive oil, rapeseed oil, groundnut oil, sunflower oil, wheat germ oil, maize germ oil, soybean oil, cottonseed oil, alfalfa oil, poppy oil, pumpkinseed oil, evening primrose oil, millet oil, barley oil, rye oil, safflower oil, candlenut oil, passionflower oil, hazelnut oil, palm oil, karite butter, apricot kernel oil, calophyllum oil, sisymbrium oil, avocado oil or calendula oil;

vegetable oils and their methyl esters which are ethoxylated;

oils of animal origin, such as squalene or squalane;

mineral oils, such as liquid paraffin, liquid petrolatum and isoparaffins;

synthetic oils, in particular fatty acid esters, such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate or propylene glycol dicaprylate, esters derived from lanolic acid, such as isopropyl lanolate or isocetyl lanolate, monoglycerides, diglycerides and triglycerides of fatty acids, such as glyceryl tri-heptanoate, alkyl benzoates, poly-α-olefins, polyolefins, such as polyisobutene, synthetic isoalkanes, such as isohexadecane or isododecane, and perfluorinated oils. Silicone oils are also capable of being used in the context of the present invention. Among the latter, mention may more particularly be made of dimethylpolysiloxanes, methylphenylpolysiloxanes, silicones modified by amines, silicones modified by fatty acids, silicones modified by alcohols, silicones modified by fatty acids and alcohols, silicones modified by polyether groups, modified epoxy silicones, silicones modified by fluorinated groups, cyclic silicones and silicones modified by alkyl groups. However, for practical reasons, it may be desirable for the fatty phase not to comprise silicone oil.

The water-in-oil emulsion generally comprises from 2 to 40% by weight, preferably from 2 to 20% by weight, of oil(s).

The fatty phase is prepared in the presence of an emulsifying system with a lipophilic nature comprising one or more emulsifying surfactants.

Mention will in particular be made, among the emulsifying surfactants capable of being used in the context of the present invention, of lipoamino acids and their salts; lipopeptides and their salts; sorbitan esters, such as, for example, the product sold under the name Montane® 80 by Seppic; polyglycerol esters, such as, for example, the products sold under the name Isolan® GI34 by BASF and Plurol® Diisostearique by Gattefosse; ethoxylated castor oil and ethoxylated hydrogenated castor oil, such as, for example, the product sold under the name Simulsol® 989 by Seppic; glyceryl stearate; polyglycol or polyglycerol polyhydroxystearates, such as, for example, the products known as Hypermer® B246 and Arlacel® P135 sold by Uniquema, the product known as Dehymuls® PGPH sold by Cognis or the product known as Decaglyn® 5HS sold by Nikko; polyethylene glycol/alkyl glycol copolymers, such as PEG-45 dodecyl glycol copolymer, for example the product sold under the name Elfacos ST 9® by Akzo, or ethoxylated sorbitan esters, such as, for example, the products sold under the name Montanox® by Seppic; slightly ethoxylated (from 1 to 3 EO groups) protein acylates; ethoxylated beeswax, such as, for example, the product known as Apifil® sold by Gattefosse; cationic emulsifiers, such as amine oxides, quaternium 82 and the surfactants disclosed in Patent Application WO 96/00719 and mainly those where the fatty chain comprises at least 16 carbon atoms; sucrose esters or methylglucoside esters which may or may not be ethoxylated; ethoxylated fatty acids; ethoxylated fatty alcohols; anionic emulsifiers, such as decyl phosphate or cetearyl sulphate; poly(oxyaluminium stearate), such as, for example, the product sold under the name Manalox® by Rhodia; magnesium stearate; or aluminium stearate.

Nonionic and anionic silicone emulsifying surfactants are also capable of being used in the context of the present invention, even if, for practical reasons (they can bring about a modification in the sensory properties of the emulsions obtained), they do not represent a preferred aspect of the invention.

It is also possible to use emulsifying surfactants of alkylpolyglycoside type, for example those disclosed in Patent Application FR-A-2 790 977, in particular xylose derivatives.

Use may also advantageously be made of an emulsifier based on alkylpolyglycosides and on fatty diols, in particular comprising:

5 to 95 parts by weight of a mixture of alkyl-polyglycosides which is composed of the reaction products of a saccharide and of a dimerdiol having 36 carbon atoms;

95 to 5 parts by weight of a dimerdiol having 36 carbon atoms.

The preferred emulsifiers corresponding to the above definition comprise:

5 to 60 parts by weight of the abovementioned mixture of alkylpolyglycosides; and 95 to 40 parts by weight of dimerdiol having 36 carbon atoms.

The mixture of alkylpolyglycosides which is composed of the reaction products of a saccharide and of a dimer-diol having 36 carbon atoms is in fact composed of a mixture in all proportions of hydroxyalkylpoly-glycosides (products resulting from the acetalization of one of the two hydroxyl groups of the dimerdiol) and of polyglycosylalkylpolyglycosides (products resulting from the acetalization of the two hydroxyl groups of the dimerdiol).

These alkylpolyglycosides can be represented respectively by the following formulae (I) and (II):

$$HO-R-O(G)_n \quad (I)$$

$$(G)_m\text{-}OR-O\text{-}(G)_p \quad (II)$$

in which:

G represents a saccharide residue;

R represents a disubstituted group derived from dimer alcohol originating from the hydrogenation of dimer acid;

n, m and p represent the mean degree of polymerization of each saccharide residue.

The product known under the name "dimer acid" is a dibasic acid having 36 carbon atoms, the predominant compound of which can be represented by the formula:

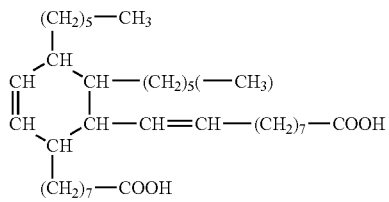

The abovementioned alkylpolyglycosides can comprise, as saccharide residue, a glucose or dextrose, fructose, galactose, mannose, ribose or xylose residue, preferably a glucose or xylose residue.

In addition, it should be noted that each unit of the polyoside part of the abovementioned alkylpoly-glycosides can be in the α or β anomeric form and the saccharide residue can be of furanoside or pyranoside type.

The mean degree of polymerization of each saccharide residue is generally between 1.05 and 2.5, preferably between 1.1 and 2.

The expression "alkylpolyglycoside" used in the context of the present application thus denotes without distinction an alkylmonooside (degree of polymerization equal to 1) or an alkylpolyglycoside (degree of polymerization of greater than 1).

The dimerdiol used for the preparation of the above emulsifying surfactant is a diol originating from the hydrogenation of dimer acid.

It is sold in particular by Cognis under the name Speziol® C 36/2.

This compound, because of its origin, can comprise minor proportions of impurities. Such impurities can be present in amounts ranging up to 30% by weight of the total weight of the diol.

Consequently, the emulsifying surfactants based on alkylpolyglycosides and on fatty diols may comprise, in corresponding minor proportions, such impurities or the reaction products of these impurities with a saccharide.

The emulsifying surfactants based on alkylpoly-glycosides and on fatty diols which can be used in the context of the present invention can be prepared by simple mixing of their constituents in desired predetermined proportions.

On the industrial scale, they will preferably be prepared according to one of the two routes conventionally used for the synthesis of alkylpoly-glycosides and, for example, by reaction, in an acid medium, between the dimerdiol and a saccharide having an anomeric OH, such as glucose or dextrose.

If appropriate, this synthesis can be supplemented by neutralization, filtration, distillation or decoloration operations or an operation in which the excess fatty diol is partially extracted.

It can also be particularly advantageous to use an emulsifying surfactant based on alkylpolyxyloside, as disclosed in Application EP-A-1 142 901, of formula:

$$R-O-(X)_p$$

in which:

p represents a decimal number between 1 and 5,

X represents the xylose residue, and

R represents a branched alkyl radical:

$$CH(C_nH_{2n+1})(C_mH_{2m+1})-CH_2-$$

in which m is an integer between 6 and 18, n is an integer between 4 and 18 and the sum n+m is greater than or equal to 14;

or else, in a particularly preferred embodiment, a composition composed of a mixture of at least two compounds as defined above;

or alternatively a composition comprising more than 0% by weight and less than 100% by weight, preferably from 1% to 60% by weight, of a compound or of a mixture of compounds defined above, and more than 0% by weight and less than 100% by weight, preferably from 40% to 99% by weight, of a compound or of a mixture of compounds of formula ROH in which R has the meaning mentioned above.

In a particularly preferred way, use is made of a mixture of alkylpolyxyloside(s) $R-O-(X)_p$ and of its (their) corresponding alcohol(s) ROH in the proportions indicated above.

According to a preferred aspect of the invention, use is made of an emulsifying system comprising at least one emulsifying surfactant chosen from alkylpolyglycosides, compositions formed of alkylpolyglycoside(s) and of fatty alcohol(s), optionally alkoxylated polyol esters (the polyols being such as polyglycols and polyglycerols and optionally other polyols), such as optionally alkoxylated polyol polyhydroxystearates (the polyols being such as polyglycols or polyglycerols), or polyethylene glycol/alkyl glycol copolymers.

More preferably still, use is made of an emulsifying system comprising an optionally alkoxylated polyglycerol ester (such as a polyglycerol polyhydroxystearate), an optionally alkoxylated polyglycol polyhydroxystearate, or a polyethylene glycol/alkyl glycol copolymer, in combination with an alkylpolyglycoside or a composition formed of alkylpolyglycoside(s) and of fatty alcohol(s).

The water-in-oil emulsion generally comprises up to 10% by weight, preferably up to 5% by weight and more preferably still from 0.5 to 5% by weight of the emulsifying system comprising one or more emulsifying surfactants.

Independently of the fatty phase, the preparation is carried out of a gelled aqueous phase comprising a polymer of polyelectrolyte type, the ionic sites of which are combined with their counterions. Mention may be made, among the polymers of polyelectrolyte type capable of being used in the context of the present invention, of:

homopolymers based on a monomer having a strong acid functional group which is partially or completely salified, homopolymers based on a monomer having a weak acid functional group which is partially or completely salified, homopolymers based on a cationic monomer,
copolymers based on at least one monomer having a strong acid functional group which is partially or completely salified, which monomer is copolymerized:
  either with at least one monomer having a weak acid functional group which is partially or completely salified,
  or with at least one neutral monomer,
copolymers based on a cationic monomer copolymerized with at least one neutral monomer,
copolymers based on at least one monomer having a weak acid functional group which is partially or completely salified, which monomer is copolymerized:
  either with at least one monomer having a weak acid functional group which is partially or completely salified,
  or with at least one neutral monomer.

In this context, the phrase "partially or completely salified" means that the strong acid or weak acid functional groups are partially or completely salified in the form in particular of the alkali metal salt, such as the sodium salt or the potassium salt, of the ammonium salt or of the amino alcohol salt, such as, for example, the monoethanolamine salt.

The strong acid functional group of the monomer can in particular be the sulphonic acid functional group or the phosphonic acid functional group, the said functional groups being partially or completely salified.

The said monomer will advantageously be chosen from styrenesulphonic acid or 2-sulphoethyl methacrylate, styrenephosphonic acid which is partially or completely salified, or 2-methyl-[(1-oxo-2-propenyl)amino]-1-propanesulphonic acid (AMPS) which is partially or completely salified in the form of the sodium salt, of the ammonium salt or of the monoethanolamine salt.

The weak acid functional group of the monomer can in particular be the partially or completely salified carboxylic acid functional group. The said monomer can in particular be chosen from acrylic acid, methacrylic acid, itaconic acid or maleic acid which is partially or completely salified in the form of the sodium salt, of the potassium salt, of the ammonium salt or of the monoethanolamine salt.

When the polymer is a copolymer based on a monomer having a partially or completely salified strong acid functional group, which monomer is copolymerized with at least one neutral monomer, the said neutral monomer is chosen in particular from acrylamide, methacrylamide, vinylpyrrolidone, 2-hydroxyethyl acrylate, 2,3-dihydroxypropyl acrylate, 2-hydroxyethyl methacrylate or 2,3-dihydroxypropyl methacrylate, or an ethoxylated derivative with a molecular weight of between 400 and 1000 of each of these hydroxylated esters, tris(hydroxymethyl)acrylamidomethane or tris(hydroxymethyl)methacrylamidomethane, or an ethoxylated derivative with a molecular weight of between 400 and 1500 of each of these amides.

The fact that the aqueous phase of the emulsions according to the present invention comprises a poly-electrolyte, the ionic sites of which are combined with their counterions, contributes to the additional input of inorganic salts not being necessary.

The abovementioned polymers can be "branched" or "crosslinked". The term "branched polymer" denotes a nonlinear polymer which has pendant chains, so as to obtain, when this polymer is dissolved in water, a high state of entanglement, resulting in very high viscosities with a low gradient. The term "crosslinked polymer" denotes a nonlinear polymer which exists in the form of a three-dimensional network which is insoluble in water but which can swell in water and which thus results in the production of a chemical gel.

When the polymer is crosslinked and/or branched, the crosslinking agent and/or the branching agent is chosen in particular from diethylene or polyethylene compounds, and very particularly from diallyloxyacetic acid or one of its salts and in particular its sodium salt, triallylamine, trimethylolpropane triacrylate, ethylene glycol dimethacrylate, diethylene glycol diacrylate, diallylurea or methylenebis(acrylamide).

The crosslinking and/or branching agent is generally used in the molar proportion, expressed with respect to the monomers employed, of 0.005% to 1%, in particular of 0.01% to 0.2% and more particularly of 0.01% to 0.1%.

Generally, the polymers of polyelectrolyte type which are suitable for the preparation of emulsions according to the present invention are therefore copolymers or homopolymers, which may or may not be crosslinked or branched, comprising monomers having a partially or completely salified strong acid or weak acid functional group or a cationic functional group.

Mention may be made, among the polymers of poly-electrolyte type which are very particularly suitable for the implementation of the process of the present invention, of derivatives of acrylamide, of acrylic acid and of vinylpyrrolidone, such as copolymers of acrylic acid and of 2-methyl-[(1-oxo-2-propenyl)amino]-1-propanesulphonic acid (AMPS), copolymers of acrylamide and of 2-methyl-[(1-oxo-2-propenyl) amino]-1-propanesulphonic acid, copolymers of 2-methyl-[(1-oxo-2-propenyl)amino]-1-propanesulphonic acid and of 2-hydroxyethyl acrylate, 2-methyl-[(1-oxo-2-propenyl)amino]-1-propanesulphonic acid homopolymer, acrylic acid homopolymer, copolymers of acryloylethyl-trimethylammonium chloride and of acrylamide, copolymers of AMPS and of vinylpyrrolidone, copolymers of acrylic acid and of alkyl acrylates, the carbonaceous chain of which comprises between ten and thirty carbon atoms, or copolymers of AMPS and of alkyl acrylates, the carbonaceous chain of which comprises between ten and thirty carbon atoms.

Such polymers are generally prepared by a reverse-phase polymerization process and are sold in particular under the names Simulgel® EG, Sepigel® 305, Simulgel® NS, Simulgel® 800 and Simulgel® A respectively by Seppic. They involve partially or completely salified forms of the acid monomers. The corresponding monomer or monomers is(are) dissolved in water drops dispersed in a fatty phase using a surfactant. In this type of polymerization, each water drop in the water-in-oil emulsion constitutes in itself a "small reactor". This system minimizes the probability of termination reactions and results in polymer chains of high molecular weight. At the end of the reaction, a hydrophilic surfactant and water are added. The polymer spreads out, no longer being constrained by the size of the water drop in which it was synthesized, resulting in a "soft solid" which is characterized by a three-dimensional structure.

This preparation process involves surfactants, such as sorbitan esters, mannitan esters, polyglycol, polyglycerol or polyol polyhydroxystearates, alkanolamides on linear or branched fatty chains, ethoxylated sorbitan esters, ethoxylated mannitan esters, ethoxylated nonylphenols or ethoxylated octylphenols. For this reason, the abovementioned surfactants may be present in the gelled aqueous phase during the implementation of the process of the invention.

Advantageously, the dry weight of the said polyelectrolyte constitutes between 0.1% and 4% and preferably between 0.5% and 2% of the weight of the aqueous phase, if the process for the preparation of such a polyelectrolyte results from a precipitating polymerization process; or the dry weight of the said polyelectrolyte constitutes between 0.25% and 4% and preferably between 0.5% and 2% of the weight of the aqueous phase, if the process for the preparation of such a polyelectrolyte results from a reverse-emulsion polymerization preparation process.

The polymers of polyelectrolyte type used in the process of the present invention have a shear-thinning (non-newtonian) behaviour, that is to say that the viscosity observed varies according to the shear gradient.

Without wishing to be committed to a specific theory, it is believed that this shear-thinning (non-newtonian) behaviour is probably related to the three-dimensional structure of the polymers of polyelectrolyte type, which also affects the physical properties of the emulsions. There thus exists a correlation between the behaviour of the polymers as regards viscosity and their ability to facilitate the formation of emulsions.

Advantageously, the polymers of polyelectrolyte type which can be used in the context of the present invention exhibit a non-newtonian rheological behaviour in solution characterized by a gradient index of between 0.1 and 0.7 and preferably between 0.2 and 0.5.

Advantageously, the gelled aqueous phase obtained by dissolving the polymer of polyelectrolyte type will exhibit a viscosity of between 0.5 and 300 Pa·s, preferably between 1.0 and 150 Pa·s and more particularly between 5 and 100 Pa·s, measured on a Brookfield LV viscometer (6 rpm, 20° C.).

The water-in-oil emulsion in accordance with the present invention can also optionally comprise up to 10% by weight of a stabilizer.

Mention may be made, among the stabilizing agents capable of being used in the context of the present invention, of hydrogenated castor oil; stearic acid and its metal salts, such as aluminium stearate; hydrophobic silicas; polymers, such as the products sold under the name Kraton® Polymers by Kraton; clays, such as hectorite or bentonite; hydrophobic modified starches, such as, for example, the product sold under the name Dry Flo PC® by National Starch; crosslinked or noncrosslinked poly(methyl methacrylate)s, such as the Micropearl products sold by Seppic; or polyamides, such as Orgasol 2002, sold by Atochem.

Waxes of vegetable, animal or mineral origin, such as beeswax, carnauba wax, candelilla wax or ozokerite, are also capable of being used in the context of the present invention, even if, for practical reasons, they do not represent a preferred aspect of the invention.

In a way known per se, these emulsions can additionally comprise one or more compounds chosen from humectants, such as, for example, glycerol, glycols or the sodium salt of 2-pyrrolidone-5-carboxylic acid, preservatives, such as, for example, the products known under the name Sepicide® and sold by Seppic, colorants, fragrances, cosmetic active principles, such as, for example, water-soluble vitamins and vitamin derivatives, fat-soluble vitamins and vitamin derivatives, oligosaccharides, proteins, polypeptides, amino acids, N-acylated derivatives of amino acids and/or of polypeptides and/or of proteins, plant extracts, marine algae extracts, inorganic or organic sunscreens, inorganic fillers, such as mica, silica and talc, synthetic fillers, such as nylons and poly(methyl methacrylate)s, which may or may not be crosslinked, silicone elastomers or sericites.

The water-in-oil emulsion can also comprise one or more electrolyte inorganic salts, such as, for example, magnesium chloride, magnesium sulphate, sodium borate or sodium chloride, in an amount ranging from 0.1% to 5% by weight.

These electrolytes are not, however, essential in producing the emulsions in accordance with the invention.

These compounds can be introduced into the aqueous phase or into the oily phase, depending on their affinity for these phases.

The emulsions according to the invention are obtained by adding the fatty phase to the aqueous phase. It is possible to carry out the addition at temperatures ranging up to 80° C. However, it is advantageous to minimize the energy expenditure represented by the heating of the phases and the emulsion will therefore preferably be prepared at a temperature of less than 55° C. More preferably still, the fatty phase will be added to the gelled aqueous phase at a temperature of between 20° C. and 35° C., that is to say at ambient temperature.

The emulsion according to the invention can be prepared by mixing the two phases at a stirring rate exceeding 1500 revolutions per minute. However, it is advantageous to minimize the energy expended in the stirring used to produce the emulsion. A stirring rate of less than 1000 revolutions per minute will therefore be preferred and a stirring rate of between 80 and 800 revolutions per minute will very particularly be preferred. More preferably still, a stirring rate of between 80 and 450 revolutions per minute, very particularly between 80 and 330 revolutions per minute, will be chosen.

The emulsions in accordance with the invention, which are stable over time, advantageously exhibit a polydispersity index of greater than 41%, preferably of greater than 45% and more preferably of greater than or equal to 51%.

In this context, the polydispersity is determined by particle size analysis on a dilute form of the emulsion using a laser particle sizer of Malvern Mastersizer type.

In particular, by the use of the operating conditions of the process of the present invention, it is possible:

- to combine the fatty and aqueous phases which are both at ambient temperature,
- to carry out this combining of phases without restriction with regard to the flow rate for introducing one phase into the other,
- to produce the emulsion with relatively gentle stirring using stirring systems of simple geometry (anchor stirrer, marine propeller, deflocculator of Rayneri type),
- to avoid the use of additional substances often essential for the preparation of W/O emulsions with a high content of aqueous phase of the prior art, such as, in particular, microcrystalline waxes and electrolyte inorganic salts.

Furthermore, in the process according to the invention, the order of addition of the phases is reversed with respect to the usual order for the preparation of an emulsion of water-in-oil (W/O) type. The fact of adding the fatty phase to the aqueous phase represents a productivity gain in itself. This is because the fatty phase is lower in volume than the aqueous phase, which can make possible the use of a single preparation vessel, and has a much lower viscosity.

The W/O emulsion in accordance with the invention can advantageously be used in a cosmetic, dermocosmetic, pharmaceutical or veterinary preparation. The W/O emulsion according to the invention can also be used in a detergent preparation.

According to a specific aspect, the W/O emulsion according to the invention is an antisun emulsion, in which one or more sunscreens (substances which make it possible to prevent ultraviolet radiation from reaching the skin of the user) is (are) incorporated in the fatty phase and/or in the gelled aqueous phase.

Antisun emulsions have to satisfy a number of criteria:
they must exhibit a satisfactory photoprotective effect. This factor is quantified by the measurement of the ability of an antisun composition to reduce the erythema brought about by ultraviolet radiation;

it is desirable for them to have properties of resistance to water, that is to say that, once spread over the skin, they retain as much as possible of their photoprotective function after swimming;

for the comfort of the user, it is also desirable for topical antisun compositions to have practical and sensory qualities. They must in particular be easy to spread and must not result in a feeling of greasiness nor be sticky.

A large number of antisun compositions have been developed based on emulsions of oil-in-water type. With enough fatty phase, this type of emulsion has the advantage of facilitating the dissolution of sunscreens, which are for the most part lipophilic or fat-dispersible organic compounds, and also makes it possible to achieve good sensory properties: soft feel and easy spreading.

However, the resistance to water of oil-in-water emulsions is low. It may consequently prove to be necessary to add additives which "structure" or "stiffen" the aqueous phase, such as poly(vinylpyrrolidone), polyacrylates, polyacrylamides, or silicone oils, which enhance the water-repelling properties of the film obtained on spreading the emulsion.

The addition of such additives is often harmful as regards the sensory properties desired.

The formulation of emulsions of water-in-oil type has therefore been envisaged. However, such emulsions exhibit the disadvantage of being difficult to spread and are perceived as greasy from a sensory viewpoint.

The present inventors have discovered that the use of emulsions of water-in-oil type according to the present invention makes it possible to respond satisfactorily to all the criteria mentioned above.

It is possible in particular to combine a high level of photoprotection with a significant resistance to water while retaining an acceptable ease of spreading and while observing other sensory parameters (nongreasy, nonsticky feel).

It is possible to use any of the oils mentioned above for the preparation of antisun emulsions according to the present invention. However, it is preferable, for this application, to use one or more synthetic oils chosen from the group consisting of fatty acid esters, such as isodecyl neopentanoate, butyl myristate, propyl myristate, cetyl myristate, isopropyl palmitate, 2-ethylhexyl palmitate, butyl stearate, hexadecyl stearate, isopropyl stearate, octyl stearate, isocetyl stearate, dodecyl oleate, hexyl laurate or propylene glycol dicaprylate, esters derived from lanolic acid, such as isopropyl lanolate or isocetyl lanolate, monoglycerides, diglycerides and triglycerides of fatty acids, such as glyceryl triheptanoate and caprylic/capric triglycerides, $C_{12}$-$C_{15}$ alkyl benzoate, diisopropyl adipate, ethylhexyl cocoate, diisopropyl or ethylhexyl adipate, diisopropyl or diethylhexyl sebacate, lauryl or myristyl lactate, and diethylhexyl maleate.

The antisun emulsions according to the present invention comprise a photoprotective system comprising one or more sunscreens which can be incorporated in the fatty phase and/or in the gelled aqueous phase. Generally, the antisun emulsions comprise approximately 2% to approximately 40% by weight, preferably approximately 5% to approximately 20% by weight, of sunscreen(s).

When the gelled aqueous phase of the emulsion comprises a (some) sunscreen(s), the latter is (are) generally directly dispersed in the gelled aqueous phase, if it (they) is (are) liquid, or, if it (they) is (are) solid, it (they) is (are) generally dispersed beforehand in a solvent, such as ethanol, or in another liquid sunscreen which dissolves it (them), before being incorporated in the aqueous gel.

The sunscreens can be organic in nature or inorganic in nature and it is possible to combine organic and inorganic sunscreens in the same antisun emulsion.

Among organic sunscreens, it is possible to distinguish the family of the benzoic acid derivatives, such as para-aminobenzoic acids (PABA), in particular monoglycerol esters of PABA, ethyl esters of N,N-propoxy-PABA, ethyl esters of N,N-diethoxy-PABA, ethyl esters of N,N-dimethyl-PABA, methyl esters of N,N-dimethyl-PABA or butyl esters of N,N-dimethyl-PABA; the family of the anthranilic acid derivatives, such as homomenthyl N-acetylanthranilate; the family of the salicylic acid derivatives, such as amyl salicylate, homomenthyl salicylate, ethylhexyl salicylate, phenyl salicylate, benzyl salicylate or p-isopropanolphenyl salicylate; the family of the cinnamic acid derivatives, such as ethylhexyl cinnamate, ethyl 4-isopropylcinnamate, methyl 2,5-diisopropylcinnamate, propyl p-methoxycinnamate, isopropyl p-methoxy-cinnamate, isoamyl p-methoxycinnamate, octyl p-methoxy-cinnamate (2-ethylhexyl p-methoxycinnamate), 2-ethoxy-ethyl p-methoxycinnamate, cyclohexyl p-methoxy-cinnamate, ethyl α-cyano-β-phenylcinnamate, 2-ethylhexyl α-cyano-β-phenylcinnamate or mono(2-ethyl-hexanoyl)glyceryl di(para-methoxycinnamate); the family of the benzophenone derivatives, such as 2,4-dihydroxy-benzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methyl-benzophenone, 2-hydroxy-4-methoxybenzophenone-5-sulphonate, 4-phenylbenzophenone, 2-ethylhexyl-4'-phenylbenzophenone-2-carboxylate, 2-hydroxy-4-(n-octyloxy)benzophenone or 4-hydroxy-3-carboxybenzo-phenone; 3-(4'-methylbenzylidene)-d,1-camphor, 3-benzylidene-d,1-camphor or camphor benzalkonium methylsulphate; urocanic acid or ethyl urocanate; the family of the sulphonic acid derivatives, such as 2-phenylbenzimidazole-5-sulphonic acid and its salts; the family of the triazine derivatives, such as hydroxyphenyl triazine, ethylhexyloxyhydroxyphenyl-4-methoxyphenyltriazine, 2,4,6-trianilino-(p-carbo-2'-ethylhexyl-1'-oxy)-1,3,5-triazine; benzoic acid, 4,4-((6-(((1,1-dimethylethyl)amino)carbonyl)phenyl)-amino)-1,3,5-triazine-2,4-diyl diimino, bis (2-ethyl-hexyl) ester; 2-phenyl-5-methylbenzoxazole, 2,2'-hydroxy-5-methylphenylbenzotriazole, 2-(2'-hydroxy-5'-(t-octyl)phenyl)benzotriazole, 2-(2'-hydroxy-5'-methylphenyl) benzotriazole; dibenzazine; dianisoylmethane, 4-methoxy-4'-(t-butyl)benzoylmethane; 5-(3,3-dimethyl-2-norbornylidene)-3-pentan-2-one; the family of the diphenylacrylate derivatives, such as 2-ethylhexyl 2-cyano-3,3-diphenyl-2-propenoate or ethyl 2-cyano-3,3-diphenyl-2-propenoate; or the family of the polysiloxanes, such as benzylidene siloxane malonate.

Among inorganic sunscreens, also known as "inorganic filters", it is possible to distinguish titanium oxides, zinc oxides, cerium oxides, zirconium oxide, yellow, red or black iron oxides, or chromium oxides. These inorganic filters may or may not be micronized, may or may not have been subjected to surface treatments and may optionally be presented in the form of aqueous or oily predispersions.

The antisun emulsions according to the present invention advantageously comprise one or more inorganic fillers in the oily phase.

The invention will be illustrated by the following examples.

EXAMPLE 1

Preparation of a W/O Emulsion

Two phases are prepared separately with the following compositions:

| Fatty phase | | |
|---|---|---|
| Alkyl polyxylosides with regard to Isofol ® 20, prepared according to EP 1 142 901 | | 1.6% |
| PEG 45 dodecyl glycol copolymer (Elfacos ® ST9) | | 0.4% |
| $C_8$-$C_{10}$ Triglyceride | | 8.0% |
| Aqueous phase | | |
| Water | q.s. | 100% |
| Glycerol | | 5% |
| Simulgel ® EG | | 2% |

The fatty phase is heated gently (50° C. max) until the mixture of the three constituents is clear. This fatty phase can be stored at ambient temperature for several days without bringing about crystallization of the various surfactants present.

The aqueous gel, comprising water, a water-soluble polymer, presented as a reverse emulsion under the trade name Simulgel® EG, and glycerol, is prepared at ambient temperature with conventional stirring for this type of preparation (Rayneri deflocculator), with a stirring rate of 300 revolutions/min, at a temperature of 18-25° C.

The fatty phase is added all at once to the gel, at ambient temperature and at a moderate stirring rate (200 to 300 revolutions/min) with a stirrer equipped with a rotor of anchor type. This stirring is then maintained for ten minutes and no cooling stage is necessary.

Furthermore, the emulsion obtained is a water-in-oil emulsion which exhibits, because of its high water content, a strong shear-thinning nature in combination with a nonsticky and fresh feel.

EXAMPLE 2

Preparation of a W/O Emulsion

The same procedure as that described in Example 1 is used in an 8 kg pilot-scale reactor equipped with a planetary mixer. The emulsification rate with such a system was 100 revolutions/min and stirring was maintained for thirty minutes after the end of the addition of the fatty phase.

EXAMPLE 3

Influence of the Energy Contributed by the Quality of the Stirring

The conditions of Example 1 were repeated, using a stirrer of rotor-stator type operating at a rate of 4000 revolutions/minute to produce the emulsion.

EXAMPLE 4

Combined Influences of the Quality of the Stirring and of the Emulsification Temperature The fatty phase is heated at 80° C. until the mixture of the three constituents is clear.

The aqueous gel, comprising water, a water-soluble polymer, presented as a reverse emulsion under the trade name Simulgel® EG, and glycerol, is prepared at ambient temperature with conventional stirring for this type of preparation (Rayneri deflocculator). It is subsequently heated to 80° C.

The fatty phase is added all at once to the gel and the stirring conditions of Example 3 were repeated.

The emulsion is subsequently cooled with moderate stirring with an anchor stirrer for 20 minutes.

The properties of the emulsions obtained according to Examples 1 to 4 are collated in Table 1.

TABLE 1

| | Example 1 | Example 2 | Example 3 | Example 4 |
|---|---|---|---|---|
| Amount manufactured | 200 g | 8 kg | 200 g | 200 g |
| Emulsification temperature | 20-25° C. | 20-25° C. | 20-25° C. | 80° C. |
| Stirring rate during the emulsification | 300 rev./min | 100 rev./min | 4000 rev./min | 4000 rev./min |
| Characteristics of the emulsion obtained/Direction (1) | W/O | W/O | W/O | W/O |
| Viscosity (2) | 55.6 Pa · s | 58.0 Pa · s | 51.2 Pa · s | 51.2 Pa · s |

(1) Method: 1 g of emulsion is diluted in 5 g of demineralized water. If the emulsion is immiscible with water, it is W/O.
(2) Method: Brookfield LV 6 rpm (at 20° C.)

Comparison of Examples 3 and 4 with Example 1 shows that the direction of the W/O emulsion and the order of magnitude of the viscosity of the emulsion obtained are similar, whatever the amount of energy supplied to the system.

Furthermore, comparison of Examples 1 and 2 shows that the extrapolation of the process to a "pilot" scale is reflected by similar performances, without significant modification in the operating conditions relating to the emulsification phase.

EXAMPLE 5

Study of the Rheological Behaviour of an Aqueous Gel which can be Used in the Context of the Present Invention The Theological behaviour of various gelled aqueous phases comprising a polymer of polyelectrolyte type was studied in the absence of an organic phase using a controlled-stress rheometer CSL500 sold by TA Instruments. The viscosity measurements are recorded at 20° C. The gradient indices, shown in Table 2, are obtained by calculation of convexity of the curve analysed according to the power law mathematical model.

TABLE 2

| Polyelectrolyte studied | Amount by dry weight in the aqueous phase (%) | Gradient index | Brookfield viscosity LV 6 rpm (Pa·s) |
|---|---|---|---|
| Copolymer of AMPS and of acrylic acid | 0.96 | 0.28 | 70 |
| Copolymer of AMPS and of acrylamide | 0.8 | 0.32 | 60 |
| Copolymer of AMPS and of hydroxyethyl acrylate | 1.06 | 0.31 | 73 |
| AMPS homopolymer | 0.95 | 0.34 | 61 |
| Copolymer of AMPS and of vinyl-pyrrolidone | 0.9 | 0.34 | 70 |
| Copolymer of acrylic acid and of $C_{10-30}$ alkyl acrylates | 0.7 | 0.4 | 69 |
| Acrylic acid homopolymer | 1.5 | 0.48 | 61 |

These results show that the aqueous gels obtained from polymers of polyelectrolyte type exhibit a shear-thinning nature. This profile is illustrated by the measurement of the gradient index.

It is observed that the gradient index is generally less than 0.5 for the gels based on polyelectrolyte polymers. Other studies, the results of which are not shown, show that the aqueous gels obtained from polyethylene glycols exhibit a gradient index close to 1, thus reflecting a virtually newtonian nature.

EXAMPLE 6

Study of the Polydispersity of an Emulsion According to the Present Invention

Two phases are prepared separately with the following compositions:

| Fatty phase | |
|---|---|
| Fluidanov ® 20X[1] (octyldodecanol polyxyloside and octyldodecanol) | 0.50% |
| Arlacel ® P 135 (PEG 1500 polyhydroxystearate) | 0.10% |
| Lanol ® 99 (isononyl isononanoate) | 4.40% |
| Aqueous phase | |
| Simulgel ® EG (sodium acrylate/sodium acryloyldimethyl-taurate/isohexadecane/Polysorbate 80) | 2.85% |
| Water | 92.15% |

[1]Prepared according to EP-A-1 142 901

These two phases were combined by following the procedure of Example 1 above.

The polydispersity of the water-in-oil emulsion obtained was measured according to the method indicated above (particle size analysis on a dilute form of the emulsion using a laser particle sizer of Malvern Mastersizer type).

The polydispersity index of the emulsion was greater than 51%. Furthermore, the gradient index of the aqueous phase of this water-in-oil emulsion was 0.28.

EXAMPLE 7

Influence of the Viscosity of the Aqueous Gel on the Direction of the Emulsion

Two phases are prepared separately with the following compositions:

| Fatty phase | | |
|---|---|---|
| Alkyl polyxylosides with regard to Isofol ® 20, prepared according to EP 1 142 901 | | 2.4% |
| PEG 45 dodecyl glycol copolymer (Elfacos ® ST9) | | 0.6% |
| $C_8$-$C_{10}$ Triglyceride | | 12.0% |
| Aqueous phase | | |
| Water | q.s. | 100% |
| Simulgel ® EG | | x% |

The conditions of Example 1 were repeated, using a stirrer of anchor type operating at a rate of 300 revolutions/minute to produce the emulsion.

The viscosity of the aqueous phase and the resulting direction of the emulsion prepared according to the procedure described above are recorded in Table 3.

TABLE 3

| Amount of Simulgel ® EG employed (1) | Amount of poly-electrolyte employed (1) | Viscosity of the aqueous phase Pa·s | Characteristics of the emulsion/ Direction (2) |
|---|---|---|---|
| 2.55% | 1.0% | >100 | W/O |
| 1.70% | 0.67% | 65 | W/O |
| 1.27% | 0.50% | 40 | W/O |
| 0.85% | 0.33% | 2.0 | W/O |
| 0.61% | 0.24% | 0.4 | O/W |

(1) Amount expressed as % by weight with respect to the total weight of the emulsion
(2) Method: 1 g of emulsion is diluted in 5 g of demineralized water. If the emulsion is immiscible with water, it is W/O.

These results show that an aqueous phase with a viscosity of less than 0.5 Pa·s does not make it possible to prepare a water-in-oil emulsion under the conditions of the invention.

EXAMPLES 8-11

Preparation of Antisun Emulsions According to the Present Invention

General Protocols for Measuring the Properties of the Antisun Emulsions

Determination of the SPF (Sun Protection Factor)

The sun protection index (PI) or sun protection factor (SPF) is defined as being equal to the ratio of the minimal erythemal dose obtained using a photoprotective product (MEDp) to the minimal erythemal dose without product (MEDnp), according to the following calculation:

$$SPF=MEDp/MEDnp$$

The MED, expressed in millijoules, corresponds to the smallest light energy resulting in a slight and even erythema with clearly defined borders.

Under the standard conditions of a test to evaluate the SPF, the volunteers invited to the laboratory read an information sheet which reminds them of the conditions of the test before signing a consent form.

In a first step, calorimetric measurements are carried out on the sites to be irradiated using a device such as the Minolta Chromameter®. This is because the skin type has to be determined, as the result of the test is highly dependent on the skin colour of the subject. Skin types are divided into six categories, type 1 corresponding to the whitest skin encountered, which burns after exposure to the sun and which does not tan at all. Type 6 corresponds to the darkest skin colourings, the people exhibiting this phototype (generally of African origin) having skin which (virtually) never burns.

Subjects of phototypes II and III, which are the most representative of the phototypes subject to a significant increase in erythema by ultraviolet radiation, are preferably chosen.

Subsequently, the antisun product is applied at the rate of 2 mg/cm² to the area to be irradiated. Control products standardized by the COLIPA (European Cosmetic Toiletry and Perfumery Association) are systematically tested simultaneously and make it possible to monitor the quality of the experiment.

Fifteen minutes after the application of the products to the skin of the volunteer, the areas concerned are irradiated using a Xenon lamp following a geometric progression with a ratio of 1.25, according to the assumed factor of the product and of the reference. The Xenon lamp can, for example, be an IDEM 3000® Arquantiel short arc lamp irradiating over a spectrum ranging from 290 to 400 nm. The infrared radiation is filtered out using a filter of UG11 type (1 mm) and the IR radiation is also removed using a water filter and ventilation. The irradiation surface area is at least 1 cm². The power of the emitter is approximately 1000 W.

A typical system comprises six orifices with independent shutters. The successive opening of each orifice at a,set time interval by the operator makes it possible to obtain a geometric progression (r=1.25) of the UV dose received by the volunteer.

At a time between 16 and 24 hours after irradiation, the non-protected Minimal Erythemal Dose (MEDnp) and the MEDs protected by the reference and by the product are read simultaneously.

Determination of the Resistance to Water of the Antisun Compositions

The persistence of an antisun product is studied by UV irradiation after a test of resistance to water. This test consists in making the volunteers take two baths of 20 minutes at 30±2° C. with an interval of 10 minutes between each bath ("standardized bath"). The first bath is taken 15 minutes after the application of the antisun composition to be tested.

The percentage of persistence is calculated according to the following formula:

% of persistence=$SPF_{wr}/SPF \times 100$ with:
SPF=dry protection index
$SPF_{wr}$=protection index determined after the test of resistance to water It is generally considered that the products exhibiting a percentage of persistence of less than 50% cannot be characterized as being resistant to water. A percentage of persistence of between 50% and 80% corresponds to an acceptable degree of resistance to water for an antisun product. On the other hand, the antisun compositions possessing a percentage of persistence of greater than or equal to 80% (and which therefore exhibit a "high resistance" to water) are particularly desired in the context of the present invention.

Sensory Evaluation

The sensory evaluation was carried out by a panel of experts (typically a jury of 20 people) which grades the following criteria over a scale ranging from 0 to 10:
Easy of spreading: very easy=10
very difficult=0
Feeling of greasiness: very greasy=10
absence of feeling of greasiness=0
Sticky effect: very sticky=10
absence of sticky effect=0

EXAMPLE 8 AND COMPARATIVE EXAMPLES 1 TO 3

An antisun emulsion having the composition shown in Table 4 was prepared according to the method described in Example 1 above, the sunscreens being incorporated in the fatty phase. The photoprotective index and the percentage of persistence with respect to water were determined according to the protocols mentioned in the preceding section. Subsequently, the sensory evaluation was carried out by a panel of experts.

At the same time, comparative examples were carried out under conditions giving rise to an oil-in-water cream gel (obtained without an emulsifying system) or to emulsions composed of an oily external phase and of a nongelled aqueous internal phase.

The comparative results are presented in Table 4.

TABLE 4

| | Example | | | |
|---|---|---|---|---|
| | Comparative Example 1 | Comparative Example 2 | Comparative Example 3 | Example 8 |
| Nature of the product obtained | O/W gel | W/O emulsion | W/O emulsion | W/O emulsion with a gelled aqueous phase |
| Emulsifying system | | | | |
| PEG 30 dipolyhydroxy-stearate | — | 0.6% | 0.6% | 0.6% |
| Fluidanov ® 20X (3) | — | 2.4% | 2.4% | 2.4% |
| Fatty phase | | | | |
| Caprylic/capric triglyceride | 12% | 12% | 12% | 12% |
| Microcrystalline wax | — | — | 5% | — |
| Screening system | | | | |
| Titanium oxide (1) | 3% | 3% | 3% | 3% |
| Zinc oxide (2) | 3% | 3% | 3% | 3% |
| Ethylhexyl salicylate | 3.5% | 3.5% | 3.5% | 3.5% |
| Ethylhexyl methoxy-cinnamate | 5.25% | 5.25% | 5.25% | 5.25% |
| Polymer | | | | |
| Simulgel ® EG | 3% | — | — | 2.1% |
| Other | | | | |

TABLE 4-continued

| | Example | | | |
|---|---|---|---|---|
| | Comparative Example 1 | Comparative Example 2 | Comparative Example 3 | Example 8 |
| additives | | | | |
| MgSO$_4$ | — | 0.7% | 0.7% | — |
| Glycerol | — | 1.5% | 1.5% | 1.5% |
| Preservatives | q.s. | q.s. | q.s. | q.s. |
| Water, q.s. for 100% | | | | |
| Stability | Granular | Instable | Stable | Stable |
| Photoprotective index | — | — | 18 +/− 3 | 18 +/− 3 |
| % of resistance to water | — | — | 65 +/− 10 | 65 +/− 10 |
| Sensory evaluation | | | | |
| Ease of spreading | | | 2 | 9 |
| Feeling of greasiness | | | 8 | 1 |
| Sticky effect | | | 8 | 0 |

(1) MT100T SUNSMART
(2) Z COTE HP1 TAYCA
(3) alkylpolyxyloside with regard to 2-octyldodecanol, prepared according to EP-A-1 142 901

It is found that only the emulsion according to the present invention (Example 8) combines performances of resistance to water with great ease of spreading, a nongreasy feel and absence of a sticky effect, with a photoprotective index similar to that of Comparative Example 3, which reflects the knowledge of the state of the art for the preparation of water-in-oil emulsions stabilized by the presence of microcrystalline waxes and not employing the process according to the present invention.

EXAMPLE 9

The antisun emulsion is produced this time with the following components:

| | | |
|---|---|---|
| 1. | Montanov ® W018[1] | 1.5% |
| 2. | PEG 45 dodecyl glycol copolymer | 0.8% |
| 3. | Diisopropyl adipate | 10% |
| 4. | Tinosorb M (50% a.m.)[2] | 20% |
| 5. | Ethylhexyl methoxycinnamate | 5% |
| 6. | Sepigel ® 305 | 2% |
| 7. | Water | q.s. for 100% |
| 8. | Additives: preservatives, fragrance, citric acid | q.s. |

[1] Isostearyl glucoside and isostearyl alcohol
[2] Dispersion comprising 50% of active material Ingredients 1 to 3 are mixed and brought to 50° C. until the mixture is clear. The other ingredients of the fatty phase 4+5 are added. A gel is formed separately with 6+7. The fatty phase is added to the gel.

In the end, a PI30 antisun emulsion is obtained which exhibits an index of resistance to water of 72%. This emulsion is light, nongreasy, nonsticky and very easy to spread. It exhibits an amount of oil of 15%; in addition, it is obtained by a process not requiring a significant energy input.

The sensory evaluation gave the following grades:
Ease of spreading: 9
Feeling of greasiness: 1
Sticky effect: 0

EXAMPLE 10 AND COMPARATIVE EXAMPLE 4

The object here is to compare emulsions according to the invention, prepared according to the procedure of Example 1, with a similar composition but not comprising lipophilic surfactants. This reference system, commonly referred to as a cream gel, is very widely encountered in the cosmetic care market as it has desired sensory characteristics. On the other hand, it is not very widely encountered in antisun applications because of its low resistance to water. The reformulation of these cream gels with the process according to the present invention, and with the involvement of a lipophilic surfactant system, makes it possible to correct the weak points and to obtain formulations combining photoprotective performance, resistance to water and pleasant sensory characteristics.

TABLE 5

| | Example | |
|---|---|---|
| | Comparative Example 4 | Example 10 |
| Name of the product obtained | O/W cream gel | W/O emulsion with a gelled aqueous phase |
| Emulsifying system | | |
| PEG 30 dipolyhydroxystearate | — | 0.4 |
| Fluidanov ® 20X | — | 1.6 |
| Fatty phase | | |
| Diisopropyl adipate | 12% | 12% |
| Screening system | | |
| Ethylhexyl salicylate | 5% | 5% |
| Ethylhexyl methoxycinnamate | 5% | 5% |
| Ethylhexyl p-dimethyl-aminobenzoate | 8% | 8% |
| Butylmethoxydibenzoylmethane | 2% | 2% |
| Polymer | | |
| Simulgel ® NS | 3% | 3% |
| Other additives | | |
| Glycerol | 1.5% | 1.5% |
| Preservatives | q.s. | q.s. |
| Water, q.s. for 100% | | |
| Stability | Stable | Stable |
| Photoprotective index | 15 +/− 3 | 25 +/− 3 |
| % of resistance to water | 18% +/− 10 | 60% +/− 10 |
| Sensory evaluation | | |
| Ease of spreading | 10 | 9 |
| Feeling of greasiness | 2 | 2 |
| Sticky effect | 0 | 0 |

EXAMPLE 11 AND COMPARATIVE EXAMPLE 5

The procedure of Example 10 and of Comparative Example 4 is repeated but with a fatty phase with a different structure and a screening system of inorganic nature.

TABLE 6

| | Example | |
|---|---|---|
| | Comparative Example 5 | Example 11 |
| Nature of the product obtained | O/W gel cream | W/O emulsion with a gelled aqueous phase |
| Emulsifying system | | |
| PEG 30 dipolyhydroxystearate | — | 0.6% |
| Fluidanov ® 20X | — | 2.4% |
| Fatty phase | | |
| Caprylic/capric triglyceride | 12% | 12% |
| Screening system | | |
| Titanium dioxide, UV-Titan M160 | 10% | 10% |
| Polymer | | |
| Simulgel ® EG | 2.1% | 2.1% |
| Other additives | | |
| Glycerol | 1.5% | 1.5% |
| Preservatives | q.s. | q.s. |
| Water, q.s. for 100% | | |
| Stability | Granular | Stable |
| Photoprotective index | — | 21 +/− 3 |
| % of resistance to water | — | 51% +/− 10 |
| Sensory evaluation | | |
| Ease of spreading | — | 7 |
| Feeling of greasiness | | 3 |
| Sticky effect | | 1 |

The process according to the invention makes it possible to incorporate a screening system of inorganic nature with a stage of gelling the aqueous phase, to achieve a water-in-oil emulsion, whereas stabilization proves to be impossible after gelling the aqueous phase, in the oil-in-water scheme, without a surfactant system as in the present invention.

GENERAL CONCLUSIONS RELATING TO EXAMPLES 8-11 AND COMPARATIVE EXAMPLES 1-5

The process for the preparation of antisun emulsions of the present invention makes it possible:

To obtain photoprotective formulations having excellent resistance to water, comparable to conventional W/O emulsion of the prior art;

Advantageously, these emulsions exhibit highly advatageous sensory characteristics similar to those of formulations of cream gel type. The latter formulations do not occur to a significant extent in the antisun field as they are not very compatible with inorganic filters, are not very effective in photoprotection and are not resistant to water.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the example above.

What is claimed is:

1. A process for the preparation of a composition in a liquid form at ambient temperature consisting of a fatty external phase and a gelled aqueous internal phase representing about 60% up to about 98% by weight of said composition, said process consisting of the steps of:
   preparing a fatty phase;
   preparing a gelled aqueous phase;
   adding said fatty phase to said gelled aqueous phase, said gelled aqueous phase being about 60% to about 98% by weight of said added phases; and
   modifying said added phases to form a water-in-oil emulsion in a liquid form at ambient temperature consisting of said fatty phase as the external phase and of said gelled aqueous as the internal phase, wherein,
   said gelled aqueous phase comprises a polyelectrolyte polymer, water, and optionally one or more sunscreens, and
   said fatty phase comprises one or more oils, a lipophilic emulsifying system comprising one or more emulsifying surfactants, and optionally one or more sunscreens.

2. The process of claim 1, wherein said emulsifying system comprises at least one emulsifying surfactant selected from the following group:
   a) alkylpolyglycosides;
   b) compositions formed of alkylpolyglycoside(s) and of fatty alcohol(s);
   c) optionally alkoxylated polyol esters; and
   d) polyethylene glycol/alkyl glycol copolymers.

3. The process of claim 1, wherein said emulsifying system further comprises:
   a) alkylpolyglycosides;
   b) compositions formed of alkylpolyglycoside(s) and of fatty alcohol(s);
   c) optionally alkoxylated polyol polyhydroxystearates; and
   d) polyethylene glycol/alkyl glycol copolymers.

4. The process of claim 1, in which the emulsifying system comprises at least one selected from the following group:
   a) an optionally alkoxylated polyglycerol ester;
   b) an optionally alkoxylated polyglycol polyhydroxystearate; and
   c) a polyethylene glycol/alkyl glycol copolymer, in combination with an alkylpolyglycoside or a composition formed of alkylpolyglycoside(s) and of fatty alcohol(s).

5. The process of claim 1, wherein said polymer is selected from the group consisting of:
   a) copolymers;
   b) homopolymers, which may or may not he crosslinked or branched, based on monomers having a partially or completely salified strong acid or weak acid functional group or a cationic functional group, wherein said monomers are selected from the group consisting of:
   1) styrenesulphonic acid;
   2) 2-sulphoethyl methacrylate;
   3) styrenephosphonic acid which is partially salified;
   4) styrenephosphonic acid which is completely salified;
   5) 2-methyl-2-[(1-oxo-2 propenyl)amino]-1-propanesulphonic acid (AMPS) which is partially salified in the form of the sodium salt, of the ammonium salt, or of the monoethanolamine salt; and
   6) 2-methyl-2-[(1-oxo-2-propenyl)amino]-1-propanesulphonic acid (AMPS) which is completely salified in the form of the sodium salt, of the ammonium salt, or of the monoethanolamine salt.

6. The process of claim 1, wherein said polymer comprises at least one member selected from the following group consisting of:
   a) copolymers of acrylic acid and of 2-methyl-2-[(1-oxo-2-propenyl)amino]- 1-propanesulphonic acid (AMPS);

b) copolymers of acrylamide and of 2-methyl-2-[(1-oxo-2-propenyl)amino]-1-propanesulphonic acid;

c) copolymers of 2-methyl-2-[(1-oxo-2-propenyl) amino]-1-propanesulphonic acid and of 2-hydroxyethyl acrylate, 2-methyl-2-[(1-oxo-2-propenyl)amino]-1-propanesulphonic acid homopolymer;

d) acrylic acid hompolymer, e) copolymers of acryloylethyltrimethylammonium chloride and of acrylamide;

f) copolymers of AMPS and of vinylpyrrolidone;

g) copolymers of acrylic acid and of alkyl acrylates, wherein the carbonaceous chain comprises between 10 and 30 carbon atoms; and h) copolymers of AMPS and of alkyl acrylates, wherein the carbonaceous chain comprises between 10 and 30 carbon atoms.

7. The process of claim 1, wherein said gelled aqueous phase comprises at least one emulsifying surfactant.

8. The process of claim 1, wherein said gelled aqueous phase is obtained by dissolving said polymer and has a resulting viscosity of between about 0.5 and about 300 Pa·s.

9. The process of claim 8, wherein said gelled aqueous phase has a viscosity of between about 1.0 and about 150 Pa·s.

10. The process of claim 9, wherein said gelled aqueous phase has viscosity of between about 5 and about 100 Pa·s.

11. The process of claim 1, wherein said fatty phase is added to said gelled aqueous phase at a temperature of less than about 55° C.

12. The process of claim 1, wherein said fatty, phase is added to said gelled aqueous phase at a temperature of between about 15° C. and about 35° C.

13. The process of claim 1, wherein, said modifying step comprises mixing said fatty phase with said gelled aqueous phase with a stirring rate of less than about 1000 revolutions per minute.

14. The process of claim 13, wherein said stirring rate is between about 80 and about 800 revolutions per minute.

15. A process for the preparation of a composition in a liquid form at ambient temperature consisting of a fatty external phase and a gelled aqueous internal phase representing about 60% up to about 98% by weight of said composition, said process consisting of the steps of:

adding a fatty phase comprising one or more oils, a lipophilic emulsifying system, and optionally one or more sunscreens to a gelled aqueous phase contained in a vessel comprising water, a polyelectrolyte polymer, and optionally one or more sunscreens, said gelled aqueous representing about 60% up to about 98% of said added phases in said vessel; and mixing said fatty phase and said gelled aqueous phase to obtain a water-in-oil emulsion in a liquid form at ambient temperature in which said fatty phase is the external phase and said gelled aqueous phase is the internal phase;

wherein said lipophilic emulsifying system comprises one or more emulsifying surfactants.

* * * * *